United States Patent
Kim et al.

(10) Patent No.: US 10,386,299 B2
(45) Date of Patent: Aug. 20, 2019

(54) APPARATUS AND METHOD FOR ACQUIRING FLUORESCENCE IMAGE

(71) Applicant: KOREA BASIC SCIENCE INSTITUTE, Daejeon (KR)

(72) Inventors: Dong Uk Kim, Daejeon (KR); Ki Soo Chang, Daejeon (KR); Geon Hee Kim, Sejong-Si (KR); Joo Ran Lee, Daejeon (KR)

(73) Assignee: KOREA BASIC SCIENCE INSTITUTE, Daejeon (KR)

( * ) Notice: Subject to any disclaimer, the term of this patent is extended or adjusted under 35 U.S.C. 154(b) by 82 days.

(21) Appl. No.: 15/660,166

(22) Filed: Jul. 26, 2017

(65) Prior Publication Data
US 2018/0217064 A1 Aug. 2, 2018

(30) Foreign Application Priority Data

Feb. 2, 2017 (KR) .................. 10-2017-0015056

(51) Int. Cl.
*G01N 21/64* (2006.01)
*G06T 5/00* (2006.01)
*G06T 5/20* (2006.01)

(52) U.S. Cl.
CPC ..... *G01N 21/6456* (2013.01); *G01N 21/6458* (2013.01); *G06T 5/002* (2013.01);
(Continued)

(58) Field of Classification Search
None
See application file for complete search history.

(56) References Cited

U.S. PATENT DOCUMENTS 5,485,530 A * 1/1996 Lakowicz .............. G01K 11/20
250/459.1
8,385,615 B2 2/2013 Levenson et al.
(Continued)

FOREIGN PATENT DOCUMENTS

JP 2005-91895 A 4/2005
JP 2016-161417 A 9/2016
(Continued)

OTHER PUBLICATIONS

Park et al., "Simultaneous multicolor imaging of wide-field epi-fluorescence microscopy with four-bucket detection", Biomedical Optics Express 2285, Jun. 1, 2016, vol. 7, No. 6, 001:10.1364/BOE.7.002285 (10 pages).

*Primary Examiner* — Edwin C Gunberg
(74) *Attorney, Agent, or Firm* — Westerman, Hattori, Daniels & Adrian, LLP

(57) ABSTRACT

Provided is a fluorescence image acquisition apparatus for acquiring fluorescence images and phase images using optical signals that are modulated at the same frequency and that have different time delays. The fluorescence image acquisition apparatus may include a light source configured to generate, at different time delays, a plurality of optical signals that are modulated at the same frequency, an illuminator configured to control paths of the plurality of modulated optical signals so that the plurality of modulated optical signals are illuminated onto a sample including a plurality of fluorescent materials, a photodetector configured to detect a plurality of fluorescence signals that are emitted from the plurality of fluorescent materials, respectively, and a controller configured to acquire a plurality of fluorescence images and a plurality of phase images from the plurality of detected fluorescence signals.

12 Claims, 15 Drawing Sheets

(52) U.S. Cl.
CPC ........ *G06T 5/20* (2013.01); *G01N 2021/6419* (2013.01); *G01N 2021/6421* (2013.01); *G01N 2201/0691* (2013.01); *G01N 2201/12* (2013.01); *G06T 2207/10064* (2013.01); *G06T 2207/10152* (2013.01); *G06T 2207/20024* (2013.01)

(56) References Cited

U.S. PATENT DOCUMENTS

| | | | |
|---|---|---|---|
| 8,885,165 | B2 | 11/2014 | Hoshishima et al. |
| 2015/0177150 | A1* | 6/2015 | Rothberg ............ C12Q 1/6869 506/2 |

FOREIGN PATENT DOCUMENTS

| | | |
|---|---|---|
| KR | 2011-0118716 A | 10/2011 |
| KR | 10-1554385 B1 | 9/2015 |
| KR | 10-1629576 B1 | 6/2016 |
| WO | 2014/057998 A1 | 4/2014 |

\* cited by examiner

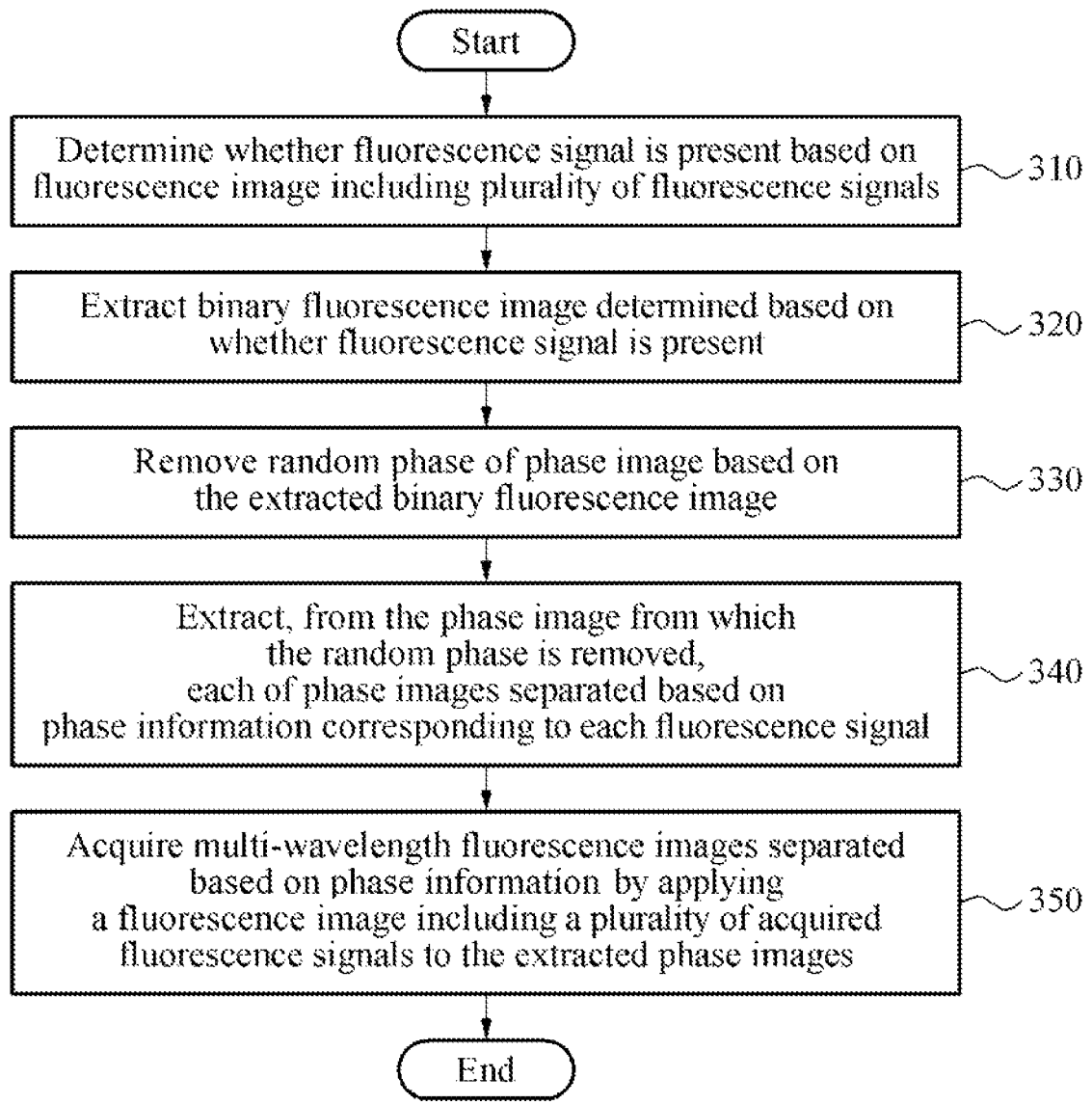

APPARATUS AND METHOD FOR ACQUIRING FLUORESCENCE IMAGE

CROSS-REFERENCE TO RELATED APPLICATION

This application claims the benefit of Korean Patent Application No. 10-2017-0015056, filed on Feb. 2, 2017, in the Korean Intellectual Property Office, the disclosure of which is incorporated herein by reference.

BACKGROUND

1. Field of the Invention

At least one example embodiment relates to an apparatus and method for acquiring a fluorescence image of a sample, and more particularly, to an apparatus and method for simultaneously detecting a plurality of fluorescence signals and acquiring fluorescence images separated for each of the fluorescence signals.

2. Description of the Related Art

Multi-wavelength fluorescence microscopy of staining regions of a sample with different fluorescent materials and detecting fluorescence signals emitted by exciting the fluorescent materials using a light source is widely used to observe a region of interest of a living cell or tissue. When the multi-wavelength fluorescence microscopy is used, temporal roles or spatial relationship of intracellular components may be observed, and an effect of monitoring a potential molecular interaction among differently stained individuals may be expected.

However, despite the development of fluorescent materials corresponding to various wavelengths, there is a limitation to fluorescence microscopy of simultaneously performing multi-wavelength fluorescence imaging due to overlapping spectra of fluorescent materials, in a related art, for example, Korean Patent Application No. 2011-0118716, Japanese Patent Application No. 2005-091895 and U.S. Pat. No. 8,385,615. Accordingly, it is necessary to use a method of removing overlapping fluorescence signals using optical filters with narrow pass bandwidths while taking into consideration a considerable loss of useful fluorescence signals for distinguishing at least two fluorescent materials with overlapping fluorescence spectra. Also, to increase a strength of a fluorescence signal, an intensity of an excitation light source may be increased. However, phototoxicity of a living sample may occur due to an increase in the intensity of the excitation light source, and accordingly there is a technical limitation to an increase in the strength of the fluorescence signal.

SUMMARY

According to an aspect, there is provided a fluorescence image acquisition apparatus for acquiring fluorescence images and phase images using optical signals that are modulated at the same frequency and that have different time delays. The fluorescence image acquisition apparatus may include a light source configured to generate, at different time delays, a plurality of optical signals that are modulated at the same frequency, an illuminator configured to control paths of the plurality of modulated optical signals so that the plurality of modulated optical signals are illuminated onto a sample including a plurality of fluorescent materials, a photodetector configured to detect a plurality of fluorescence signals that are emitted from the plurality of fluorescent materials, respectively, and a controller configured to acquire a plurality of fluorescence images and a plurality of phase images from the plurality of detected fluorescence signals.

The controller may be configured to acquire a fluorescence image including the plurality of fluorescence signals and a phase image corresponding to the fluorescence image based on a four-bucket scheme using a frame rate that varies depending on the modulation frequency. The controller may be configured to extract a phase image corresponding to each of a plurality of pieces of phase information included in the plurality of fluorescence signals.

The controller may be configured to acquire a phase image corresponding to each of the plurality of fluorescence signals and configured to separate the fluorescence images for each wavelength corresponding to each of the fluorescence signals based on a fluorescence image including the plurality of fluorescence signals.

The photodetector may be configured to detect the plurality of fluorescence signals based on a frame rate of 4f when the modulation frequency is f.

The illuminator may be configured to separate, using a polychroic mirror, the plurality of modulated optical signals generated by the light source and a plurality of fluorescence signals that are emitted from the sample.

According to another aspect, there is provided a method of separating fluorescence images based on phase images. The method may include determining whether a fluorescence signal is present, based on a fluorescence image including a plurality of fluorescence signals, extracting a binary fluorescence image determined based on whether the fluorescence signal is present, removing a random phase of a phase image based on the extracted binary fluorescence image, extracting, from the phase image from which the random phase is removed, each of phase images separated based on phase information corresponding to each of the fluorescence signals, and acquiring multi-wavelength fluorescence images separated based on phase information by applying a fluorescence image including a plurality of fluorescence signals to the extracted phase images.

The fluorescence image including the plurality of fluorescence signals may be acquired by detecting fluorescence signals generated by illuminating, at different time delays, a plurality of optical signals modulated at the same frequency onto a sample including a plurality of fluorescent materials.

According to still another aspect, there is provided a method of processing fluorescence images. The method may include generating, at different time delays, a plurality of optical signals that are modulated at the same frequency, controlling paths of the plurality of modulated optical signals so that the plurality of modulated optical signals are illuminated onto a sample including a plurality of fluorescent materials, detecting a plurality of fluorescence signals that are emitted from the plurality of fluorescent materials, respectively, and acquiring a plurality of fluorescence images and a plurality of phase images from the plurality of detected fluorescence signals.

The method may further include acquiring the plurality of fluorescence images and the plurality of phase images based on a four-bucket method scheme using a frame rate that varies depending on the modulation frequency.

The method may further include separating fluorescence images for each wavelength corresponding to each of the plurality of phase images from the plurality of fluorescence images.

Additional aspects of example embodiments will be set forth in part in the description which follows and, in part, will be apparent from the description, or may be learned by practice of the disclosure.

BRIEF DESCRIPTION OF THE DRAWINGS

These and/or other aspects, features, and advantages of the invention will become apparent and more readily appreciated from the following description of example embodiments, taken in conjunction with the accompanying drawings of which:

FIG. 3 is a flowchart illustrating a method of separating fluorescence images according to an example embodiment;

DETAILED DESCRIPTION

Figure 1:
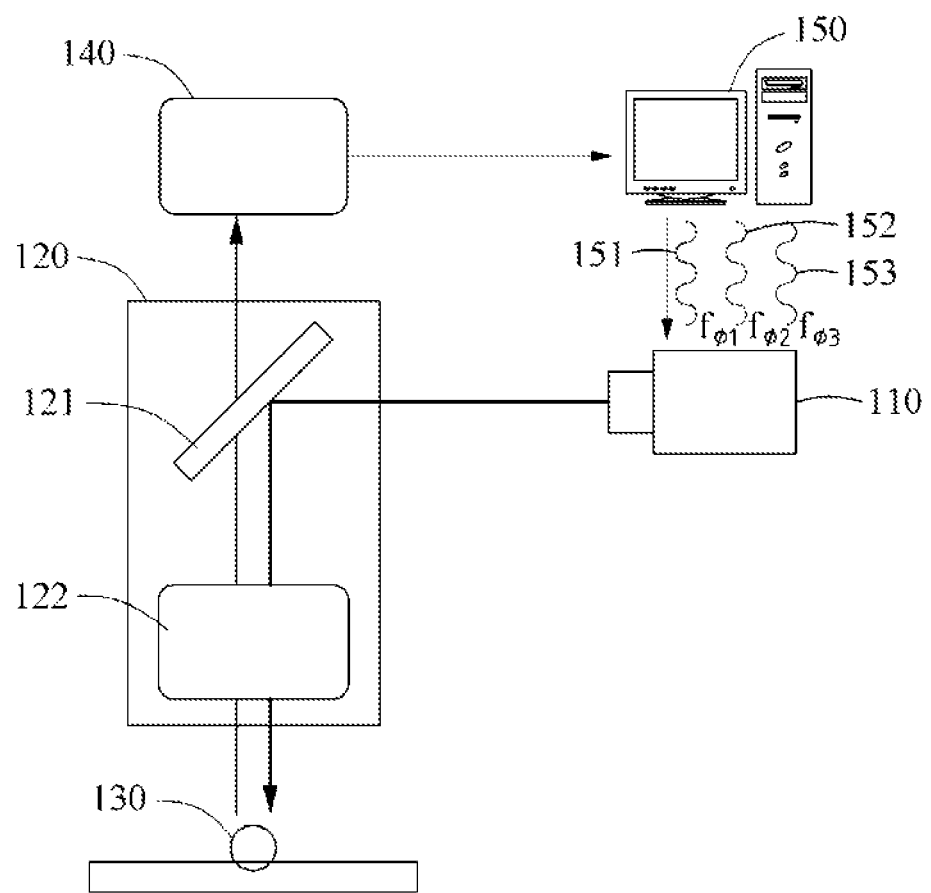
FIG. 1 is a diagram illustrating an example of a fluorescence image acquisition apparatus according to an example embodiment.

The following structural or functional descriptions of example embodiments described herein are merely intended for the purpose of describing the example embodiments described herein and may be implemented in various forms. Here, the example embodiments are not construed as limited to the disclosure and should be understood to include all changes, equivalents, and replacements within the technical idea of the present disclosure.

Hereinafter, example embodiments will be described in detail with reference to the accompanying drawings. Regarding the reference numerals assigned to the elements in the drawings, it should be noted that the same elements will be designated by the same reference numerals, wherever possible, even though they are shown in different drawings. Also, in the description of example embodiments, detailed description of well-known related structures or functions will be omitted when it is deemed that such description will cause ambiguous interpretation of the present disclosure.

FIG. 1 is a diagram illustrating an example of a fluorescence image acquisition apparatus according to an example embodiment. Referring to FIG. 1, the fluorescence image acquisition apparatus may include a light source 110, an illuminator 120, a photodetector 140 and a controller 150.

The light source 110 may generate optical signals with various wavelengths and bandwidths. A cell of the sample 130 or a region of interest of the sample 130 may be stained with fluorescent material. When an optical signal is illuminated onto the sample 130, a fluorescent material may be excited by the optical signal. Based on the above excitation, a fluorescence signal may be generated.

The controller 150 may apply a plurality of modulation signals, for example, modulation signals 151, 152 and 153, to the light source 110. The light source 110 may modulate optical signals based on the modulation signals 151, 152 and 153. For example, the light source 110 may generate a plurality of optical signals modulated at the same frequency (for example, frequencies $f_{\varphi 1}$, $f_{\varphi 2}$ and $f_{\varphi 3}$) at different time delays. The plurality of modulated optical signals may have different wavelengths. Although, in the above description, the frequencies $f_{\varphi 1}$, $f_{\varphi 2}$ and $f_{\varphi 3}$ with three different time delays are used, this is merely an example to facilitate understanding of example embodiments and will not be interpreted to limit the scope of example embodiments. For example, it is possible to implement an example in which the light source 110 generates a plurality of modulated optical signals based on a plurality of modulation signals with four different time delays.

The illuminator 120 may change paths of the plurality of modulated optical signals so that the plurality of modulated optical signals may be illuminated onto the sample 130 that includes a plurality of fluorescent materials. For example, the illuminator 120 may change the paths of the plurality of modulated optical signals generated by the light source 110 so that the plurality of modulated optical signals may be illuminated onto the sample 130 in a wide-field illumination mode. For example, the plurality of modulated optical signals may be illuminated onto the sample 130 through a dichroic mirror 121 and an object lens 122. Also, the illuminator 120 may separate the plurality of modulated optical signals from the light source 110 and fluorescence signals from the sample 130, using the dichroic mirror 121 or the polychroic mirror. The illuminator 120 may use a beam splitter to change the paths of the plurality of modulated optical signals.

A first fluorescent material among the plurality of fluorescent materials included in the sample 130 may be excited by absorbing a first modulated optical signal among the plurality of modulated optical signals illuminated onto the sample 130. For example, each of the plurality of fluorescent materials may be excited by absorbing an arbitrary optical signal among the plurality of modulated optical signals. Based on excitation, the first fluorescent material may emit a fluorescence signal and the emitted fluorescence signal may be modulated after an arbitrary time delay based on a modulation frequency of the first modulated optical signal absorbed by the first fluorescent material.

The photodetector 140 may detect a plurality of fluorescence signals generated by illuminating the plurality of modulated optical signals onto the sample 130. In an example, when the modulation frequency is f the photodetector 140 may detect a plurality of fluorescence signals using a frame rate of 4f.

In another example, the photodetector 140 may detect a plurality of fluorescence signals using a multi-point photodetector. The multi-point photodetector may be, for example, a photodetector with a one-dimensional (1D) or two-dimensional (2D) arrangement of detection regions. The multi-point photodetector may include, for example, a charge-coupled device (CCD) camera. When the photodetector 140 is implemented as a CCD camera, an image may be acquired by a single detection due to a 2D arrangement of detection regions.

The controller 150 may acquire fluorescence images and phase images from the plurality of detected fluorescence signals. Also, the controller 150 may separate the fluorescence images for each wavelength from a fluorescence image including the plurality of fluorescence signals, based on the acquired phase images. In an example, the controller 150 may acquire a fluorescence image including a plurality of fluorescence signals and a phase image corresponding to the fluorescence image, based on a four-bucket scheme. For example, the controller 150 may calculate each of a plurality of pieces of phase information included in the plurality of modulated optical signals as one of a plurality of phase images.

For example, a fluorescence signal I(x,y,t) detected by the photodetector 140 may be expressed as shown in Equation 1 below.

$$I(x,y,t) = I_{dc}(x,y) + \Delta I(x,y)\sin(2\pi f t + \phi_0) \quad \text{[Equation 1]}$$

In Equation 1, $I_{dc}$ denotes a magnitude of a fluorescence signal that is not modulated, $\Delta I$ denotes a magnitude of a modulated fluorescence signal, f denotes a modulation frequency, and $\phi_0$ denotes a phase of a modulation signal. A plurality of fluorescence signals that are modulated at the same frequency and have different time delays will be further described with reference to the following drawings.

Figure 2A:
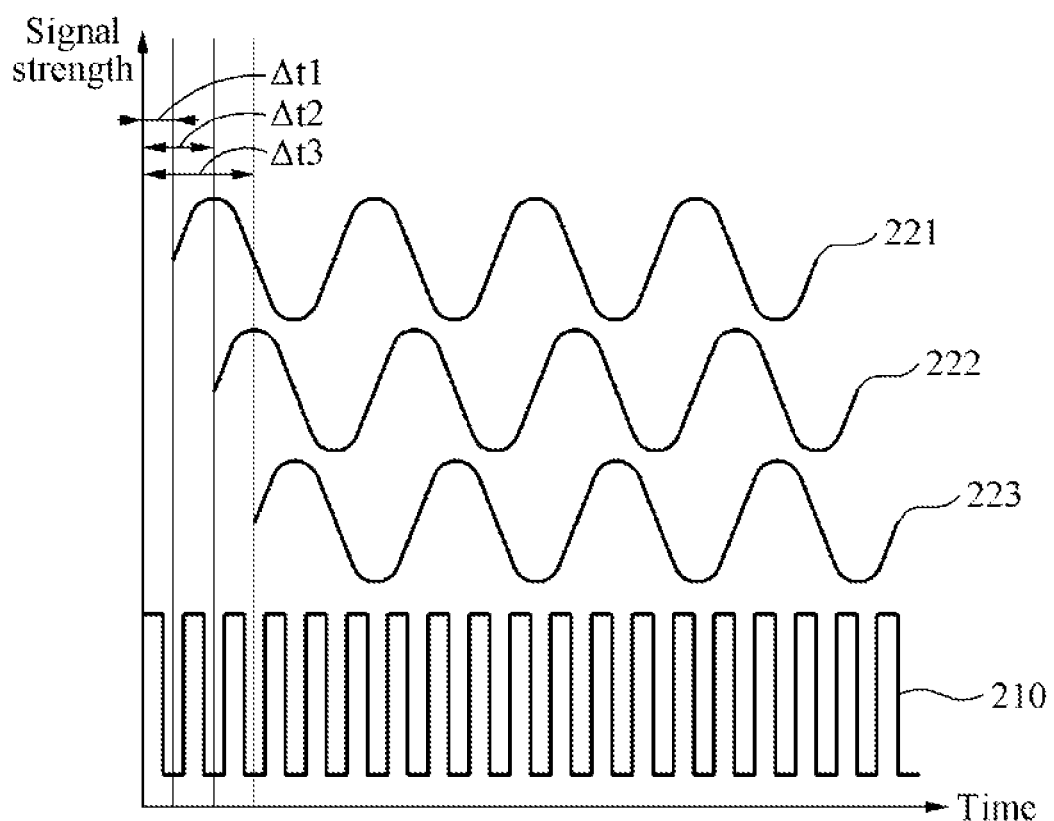
FIG. 2A is a diagram illustrating an example of a plurality of fluorescence signals that are modulated at the same frequency and that have different time delays according to an example embodiment.

FIG. 2A is a diagram illustrating an example of a plurality of fluorescence signals that are modulated at the same frequency and that have different time delays according to an example embodiment. FIG. 2A illustrates a plurality of fluorescence signals, for example, fluorescence signals 221, 222 and 223, that are generated by the excitation of each of a plurality of modulated optical signals generated by a light source. The fluorescence signals 221, 222 and 223 may have three different time delays (for example, $\Delta t1$, $\Delta t2$ and $\Delta t3$). For example, when the fluorescence signals 221, 222 and 223 are generated from a plurality of optical signals modulated at the same frequency (for example, a frequency f), a photodetector may receive an external trigger signal 210 to detect the fluorescence signals 221, 222 and 223 based on a frame rate of 4f.

Figure 2B:
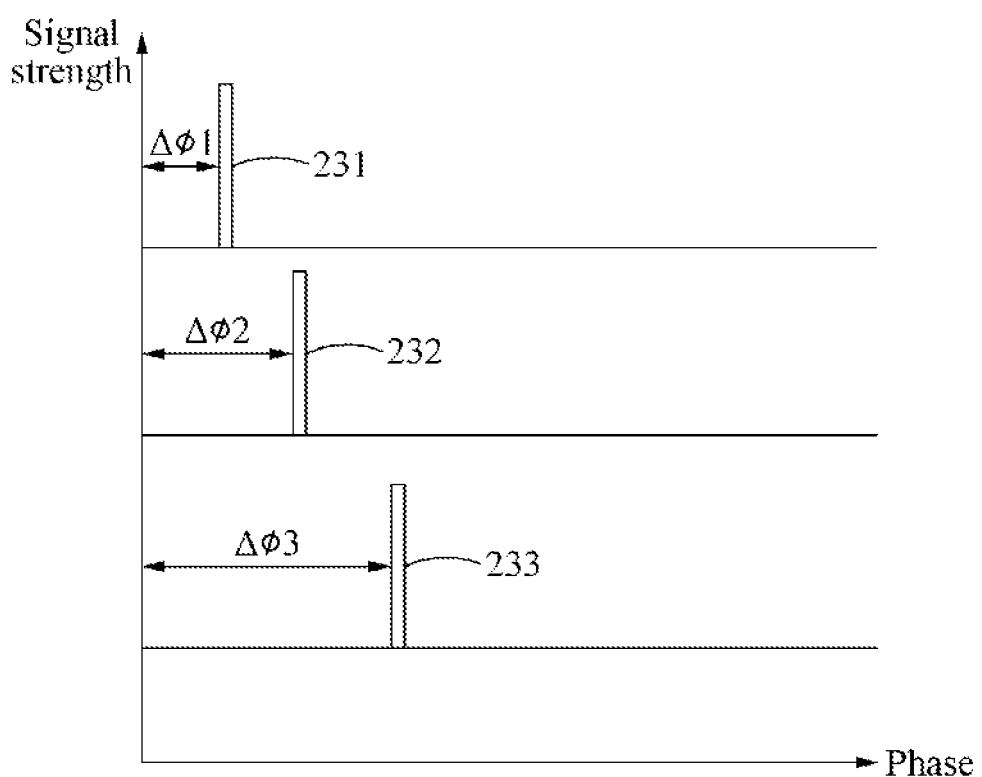
FIG. 2B is a diagram illustrating an example of the plurality of fluorescence signals of FIG. 2A in a phase domain.

FIG. 2B is a diagram illustrating an example of the plurality of fluorescence signals of FIG. 2A in a phase domain. In FIG. 2B, the fluorescence signals 221, 222 and 223 of FIG. 2A with the time delays $\Delta t1$, $\Delta t2$ and $\Delta t3$ are respectively illustrated as three phase signals, for example, phase signals 231, 232 and 233 with different phase delays (for example, $\Delta\phi1$, $\Delta\phi2$ and $\Delta\phi3$) in the phase domain.

The photodetector may acquire images $I_1$, $I_2$, $I_3$ and $I_4$ that represent magnitudes of the fluorescence signals 221, 222 and 223 that are modulated, using a preset frame rate, as shown in Equations 2 through 5 below, respectively.

$$I_1(x,y,t) = \int_0^{T/4} I(x,y,t)dt \quad \text{[Equation 2]}$$

$$I_2(x,y,t) = \int_{T/4}^{T/2} I(x,y,t)dt \quad \text{[Equation 3]}$$

$$I_3(x,y,t) = \int_{T/2}^{3T/4} I(x,y,t)dt \quad \text{[Equation 4]}$$

$$I_4(x,y,t) = \int_{3T/4}^{T} I(x,y,t)dt \quad \text{[Equation 5]}$$

In Equations 2 through 5, T denotes a period of a modulation signal, and may be defined to have a reciprocal relationship with the modulation frequency f.

A controller included in a fluorescence image acquisition apparatus may acquire a fluorescence image including a plurality of fluorescence signals and a phase image corresponding to the fluorescence image using a four-bucket scheme, using Equations 6 and 7 shown below.

$$\Delta I(x, y) = \frac{\pi}{T\sqrt{2}}\sqrt{(I_1 - I_3)^2 + (I_2 - I_4)^2} \quad \text{[Equation 6]}$$

$$\phi_0(x, y) = \tan^{-1}\left(\frac{I_1 - I_3 - (I_2 + I_4)}{I_1 - I_3 + I_2 - I_4}\right) \quad \text{[Equation 7]}$$

FIG. 3 is a flowchart illustrating a method of separating fluorescence images according to an example embodiment. Referring to FIG. 3, the method may include operation 310 of determining whether a fluorescence signal is present based on a fluorescence image including a plurality of fluorescence signals, operation 320 of extracting a binary fluorescence image determined based on whether the fluorescence signal is present, operation 330 of removing a random phase of a phase image based on the extracted binary fluorescence image, operation 340 of extracting, from the phase image from which the random phase is removed, each of phase images separated based on phase information corresponding to each of the fluorescence signals, and operation 350 of acquiring multi-wavelength fluorescence images separated based on phase information by applying a fluorescence image including a plurality of acquired fluorescence signals to the extracted phase images.

In operation 310, a fluorescence image acquisition apparatus may determine whether a fluorescence signal is present, based on a fluorescence image that includes a plurality of fluorescence signals. The fluorescence signal may be generated by illuminating, at different time delays, a plurality of optical signals modulated at the same frequency onto a sample including a plurality of fluorescent materials. Also, a fluorescence signal may be modulated after an arbitrary time delay based on the same modulation frequency of the modulated optical signals absorbed by the plurality of fluorescent materials.

In operation 320, the fluorescence image acquisition apparatus may extract a binary fluorescence image determined based on whether the fluorescence signal is present. For example, the fluorescence image acquisition apparatus may extract the binary fluorescence image using a scheme of assigning a first binary number to a pixel in which a fluorescence signal is present in an entire image and assigning a second binary number to a pixel in which the fluorescence signal is absent in the image.

In operation 330, the fluorescence image acquisition apparatus may remove a random phase of a phase image based on the extracted binary fluorescence image. For example, the fluorescence image acquisition apparatus may multiply the phase image by the extracted binary fluorescence image to remove the random phase.

In operation 340, the fluorescence image acquisition apparatus may extract each of phase images separated based on phase information corresponding to each of the fluorescence signals from the phase image from which the random phase is removed.

In operation 350, the fluorescence image acquisition apparatus may acquire multi-wavelength fluorescence images separated based on phase information by applying a fluorescence image including a plurality of acquired fluorescence signals to the extracted phase images. For example, the fluorescence image acquisition apparatus may multiply each of extracted phase images by the fluorescence image including the plurality of fluorescence signals, and may acquire fluorescence images separated for each wavelength based on the phase information.

FIGS. 4A through 4F illustrate examples of multi-wavelength fluorescence images acquired by a fluorescence image acquisition apparatus according to an example embodiment. A fluorescent bead sample may be made using both a first fluorescent bead and a second fluorescent bead that have different fluorescence spectra. For example, the first fluorescent bead may be a yellow-green fluorescent bead, and the second fluorescent bead may be an orange fluorescent bead.

Figure 4A:
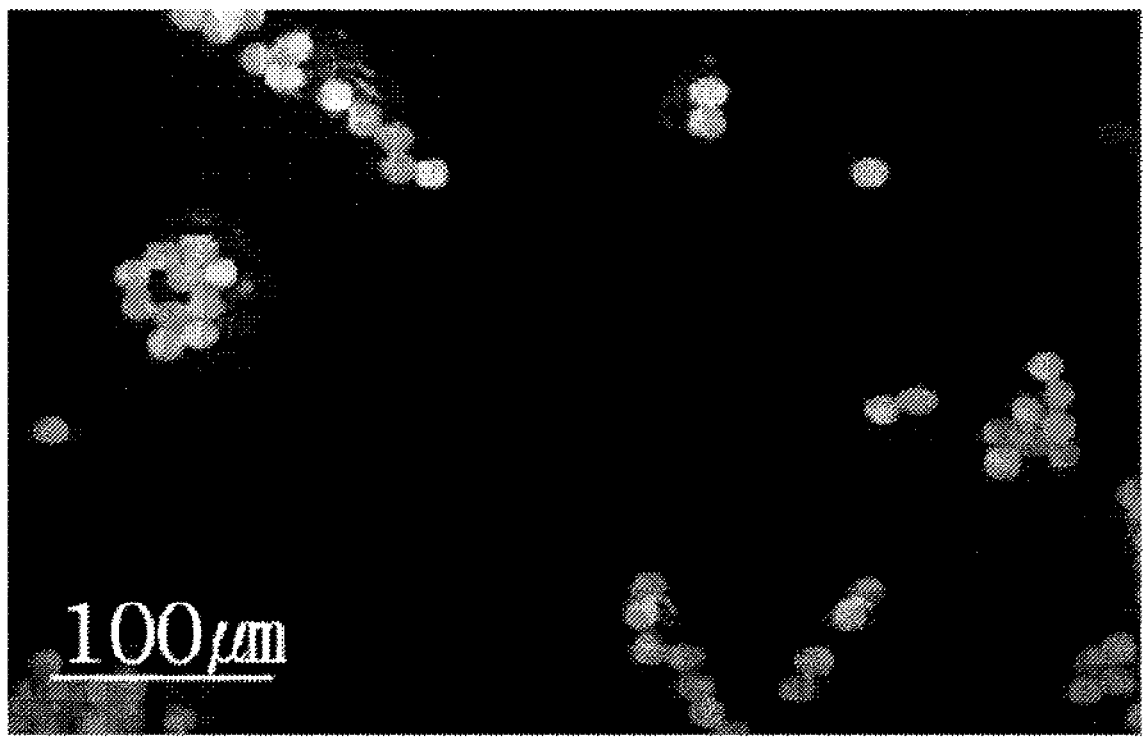
FIGS. 4A through 4F illustrate examples of multi-wavelength fluorescence images acquired by a fluorescence image acquisition apparatus according to an example embodiment.
Figure 4B:
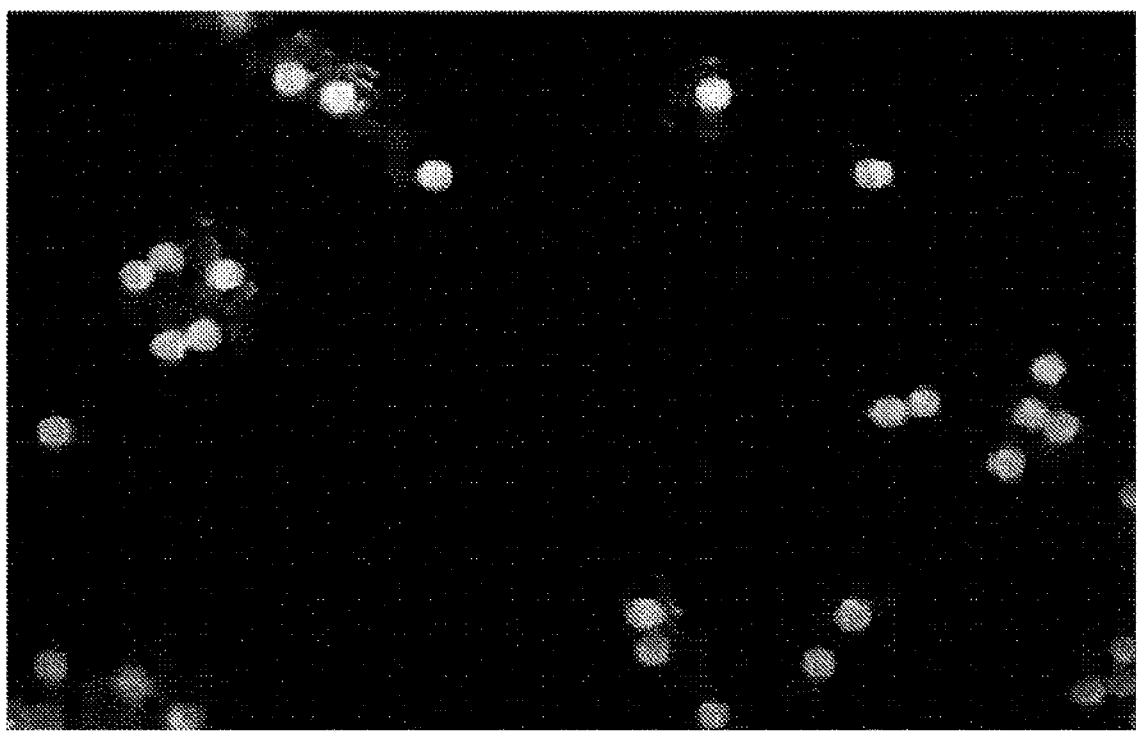
Figure 4C:
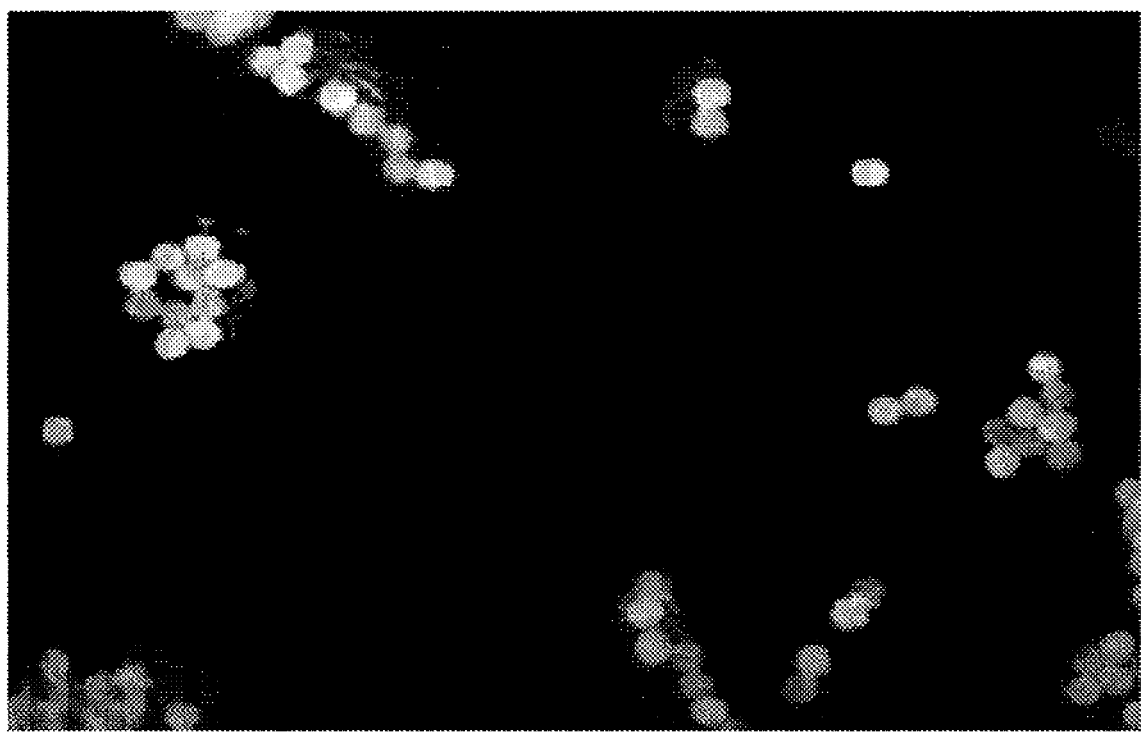
Figure 4D:
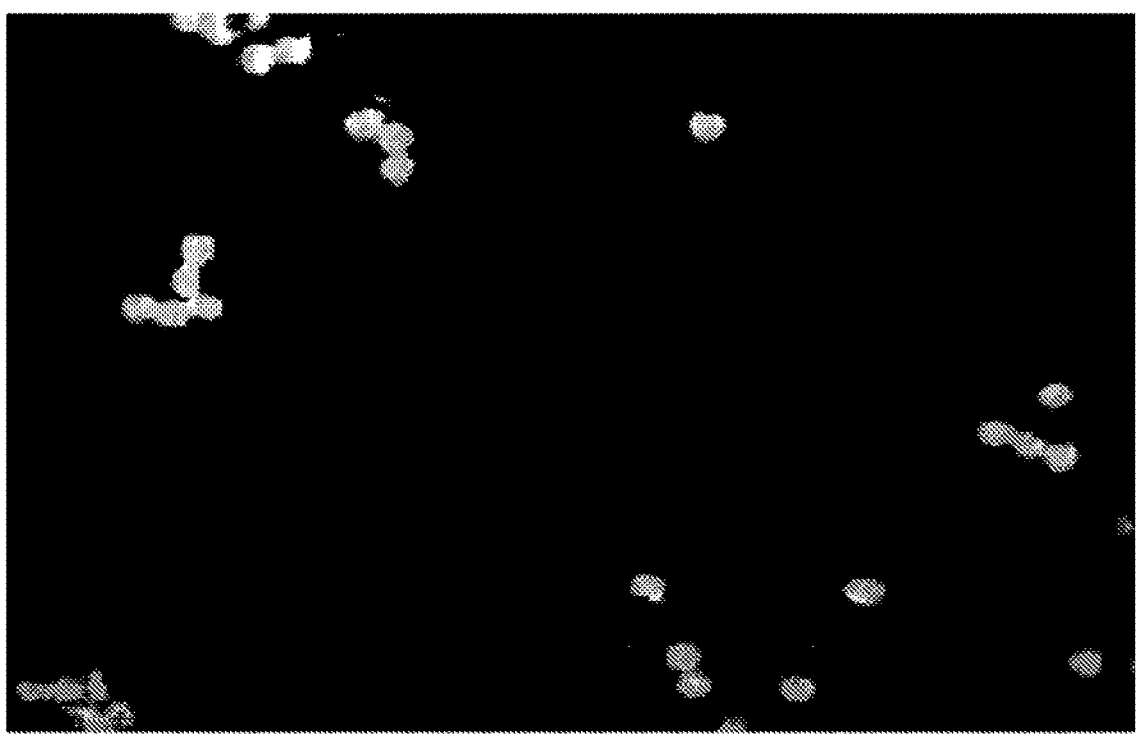
Figure 4E:
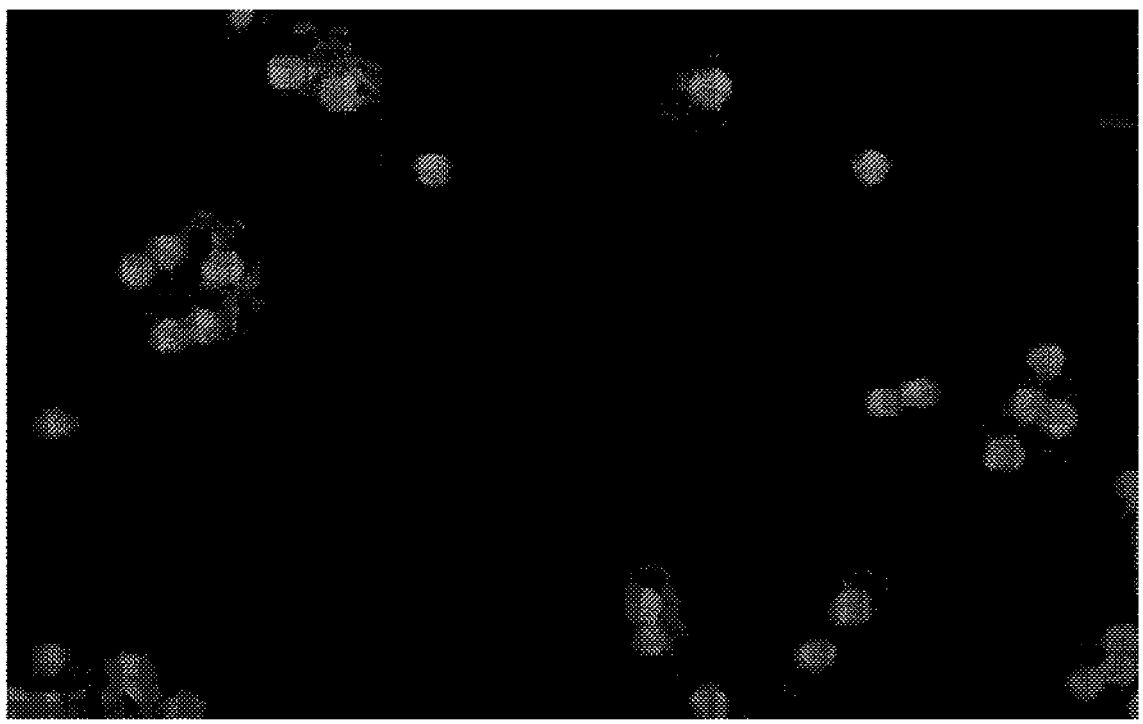
Figure 4F:
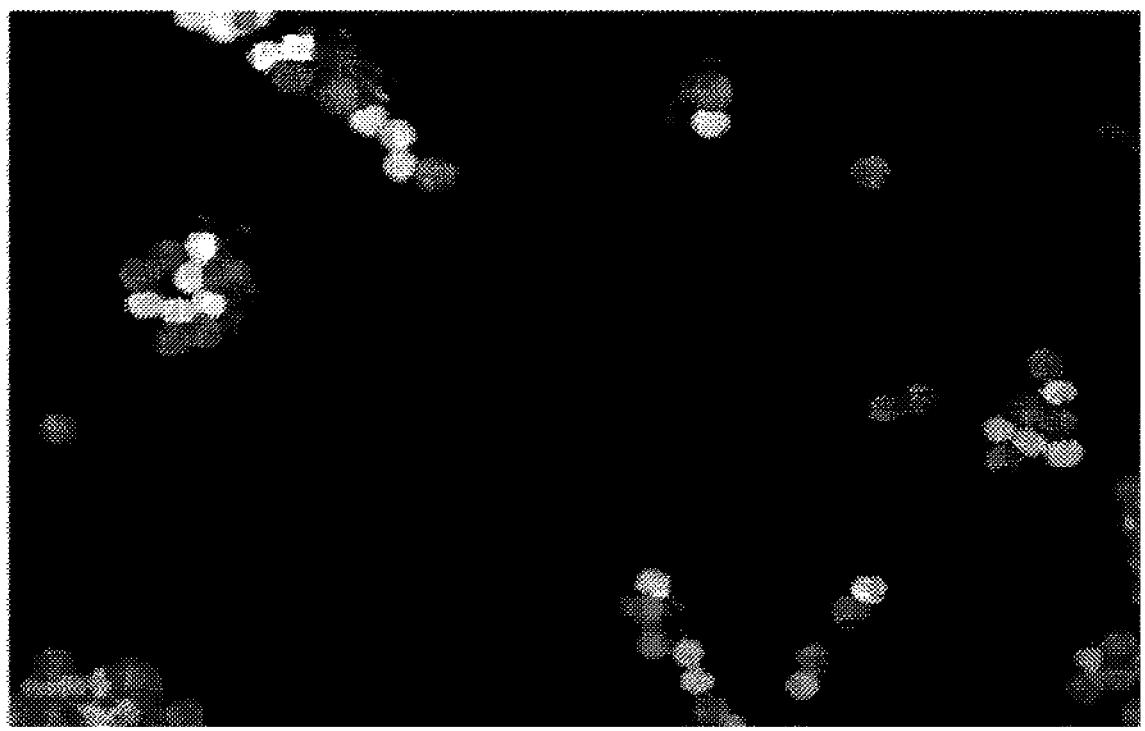
Figure 5:
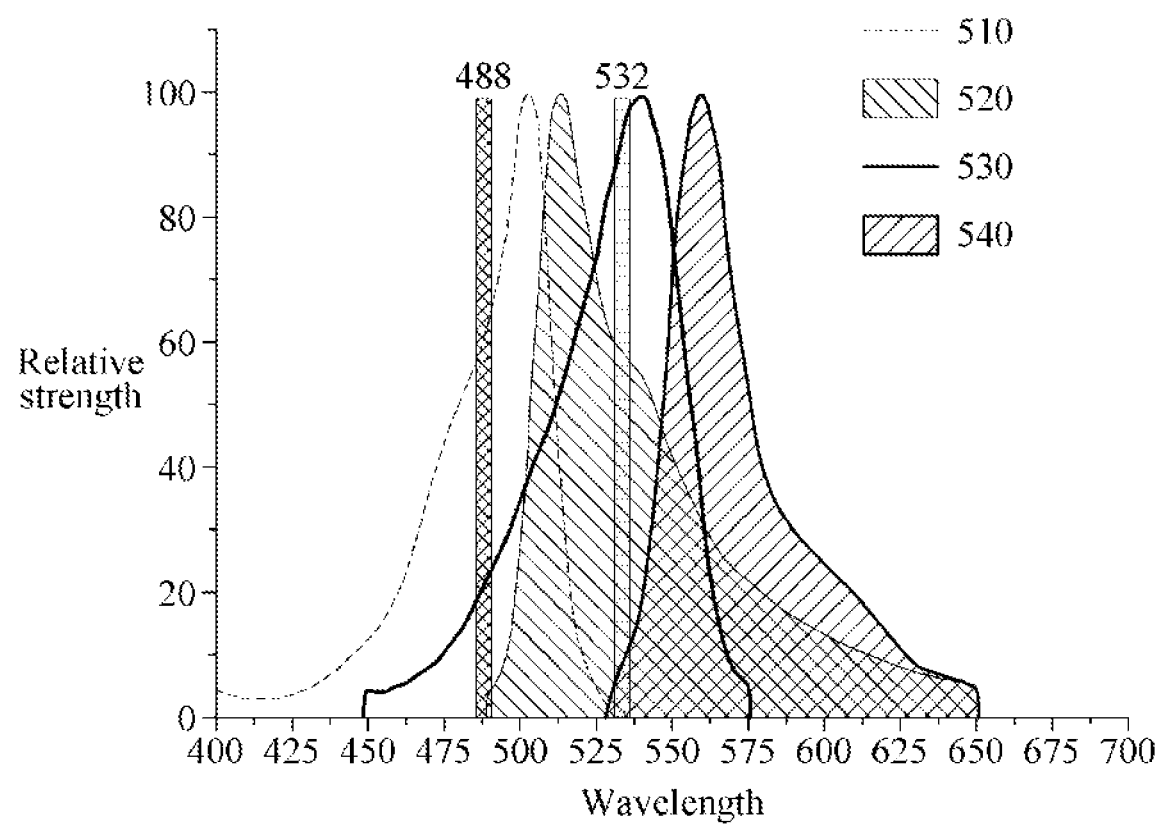
FIG. 5 illustrates spectra of two fluorescent beads excited by two laser light sources that respectively correspond to wavelengths of 488 nanometers (nm) and 532 nm according to an example embodiment.

FIG. 5 illustrates spectra of two fluorescent beads excited by two laser light sources that respectively correspond to wavelengths of 488 nm and 532 nm according to an example embodiment. A first fluorescent bead and a second fluorescent bead having spectral characteristics shown in FIG. 5 may be used to derive results of examples described with reference to FIGS. 4A through 4F. In FIG. 5, a region indicated by a line 510 represents an absorption spectrum of a yellow-green fluorescent bead, and a region 520 represents an emission spectrum of the yellow-green fluorescent bead. Also, a region indicated by a line 530 represents an absorption spectrum of an orange fluorescent bead, and a region 540 represents an emission spectrum of the orange fluorescent bead.

FIGS. 4A and 4B illustrate fluorescence images of two fluorescent beads acquired based on a four-bucket scheme after exciting a sample independently using a first laser light source with a wavelength of 488 nm and a second laser light source with a wavelength of 532 nm. FIG. 4C illustrates a fluorescence image acquired based on the four-bucket scheme after exciting a sample using both the first laser light source and the second laser light source. Because the two fluorescent beads are simultaneously excited by the first laser light source as shown in absorption spectra of the two fluorescent beads, the fluorescence images of FIGS. 4A and 4C may be very similar to each other.

FIGS. 4D and 4E illustrate multi-wavelength fluorescence images for two fluorescent beads acquired using a method of separating fluorescence images according to an example embodiment. FIG. 4F illustrates a plurality of fluorescence images acquired by superimposing the fluorescence images of FIGS. 4D and 4E. The multi-wavelength fluorescence image of FIG. 4D acquired using a method of acquiring multi-wavelength fluorescence images according to an example embodiment may accurately represent a single fluorescent bead even though an additional fluorescence filter is not used, unlike FIG. 4A.

FIGS. 6A through 6D illustrate examples of multi-wavelength fluorescence images acquired by a fluorescence image acquisition apparatus according to a related art, and FIGS. 6E through 6H illustrate examples of fluorescence images illustrating examples of multi-wavelength fluorescence images acquired by a fluorescence image acquisition apparatus according to an example embodiment.

Figure 6A:
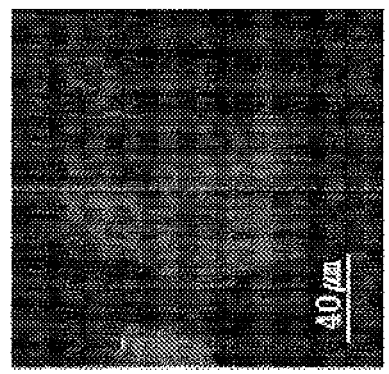
FIGS. 6A through 6D illustrate examples of multi-wavelength fluorescence images acquired by a fluorescence image acquisition apparatus according to a related art.
Figure 6B:
Figure 6C:
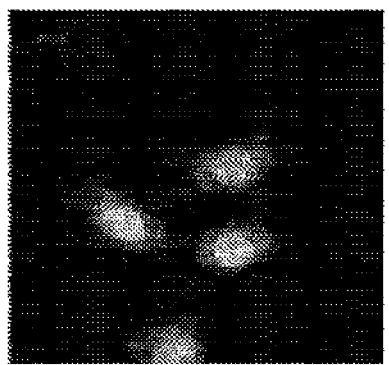
Figure 6D:
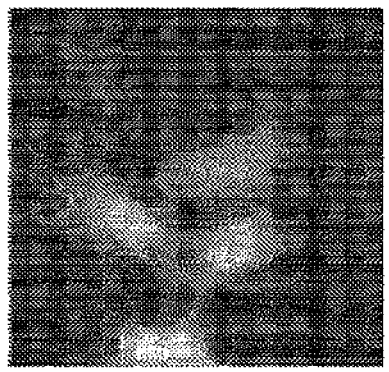
Figure 6E:
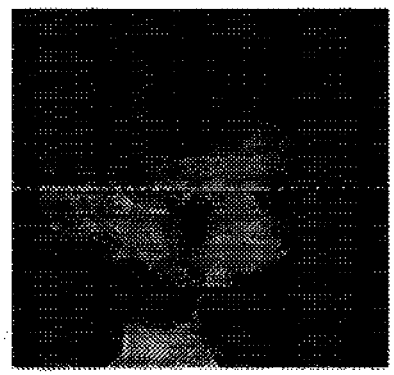
FIGS. 6E through 6H illustrate examples of multi-wavelength fluorescence images acquired by a fluorescence image acquisition apparatus according to an example embodiment.
Figure 6F:
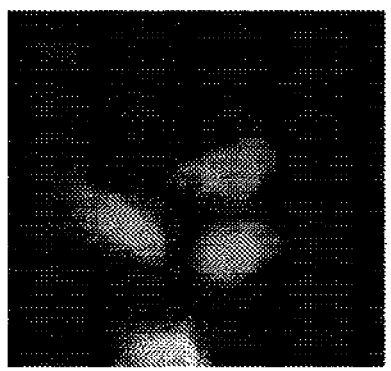
Figure 6G:
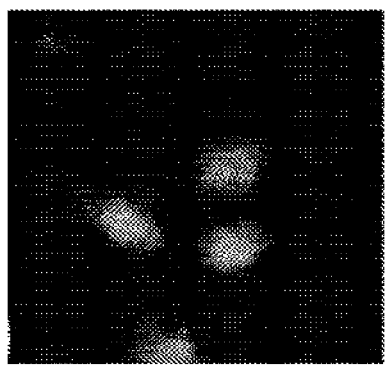
Figure 6H:

FIGS. 6A through 6H illustrate a result of an experiment to acquire a multi-wavelength fluorescence image associated with a cell stained with a fluorescent material with overlapping fluorescence spectra. In a HeLa cell sample, an actin, a mitochondria and a nucleus are stained using Alexa Fluo 488 Phalloidin, MitoTracker Red CMXRos and To-Pro-3 Iodide. FIGS. 6A and 6E illustrate images associated with the actin, and FIGS. 6B and 6F illustrate images associated with the mitochondria. Also, FIGS. 6C and 6G illustrate images associated with the nucleus, and FIGS. 6D and 6H illustrate merged images including the actin, the mitochondria and the nucleus.

Referring to FIGS. 6A through 6C, fluorescence images representing the actin, the mitochondria and the nucleus are acquired based on a wide-field illumination fluorescence microscopy using a specific fluorescence bandpass filter according to the related art. Referring to FIGS. 6E through 6G, multi-wavelength fluorescence images representing the stained regions are acquired based on a fluorescence image acquisition method according to an example embodiment. Comparison between the fluorescence images of FIGS. 6A through 6C and the fluorescence images of FIGS. 6E through 6G shows that a fluorescence image acquisition apparatus to which a four-bucket scheme and a method of separating fluorescence images are applied may separate independent fluorescence images for each wavelength from a fluorescence image including a plurality of fluorescence signals.

Figure 7:
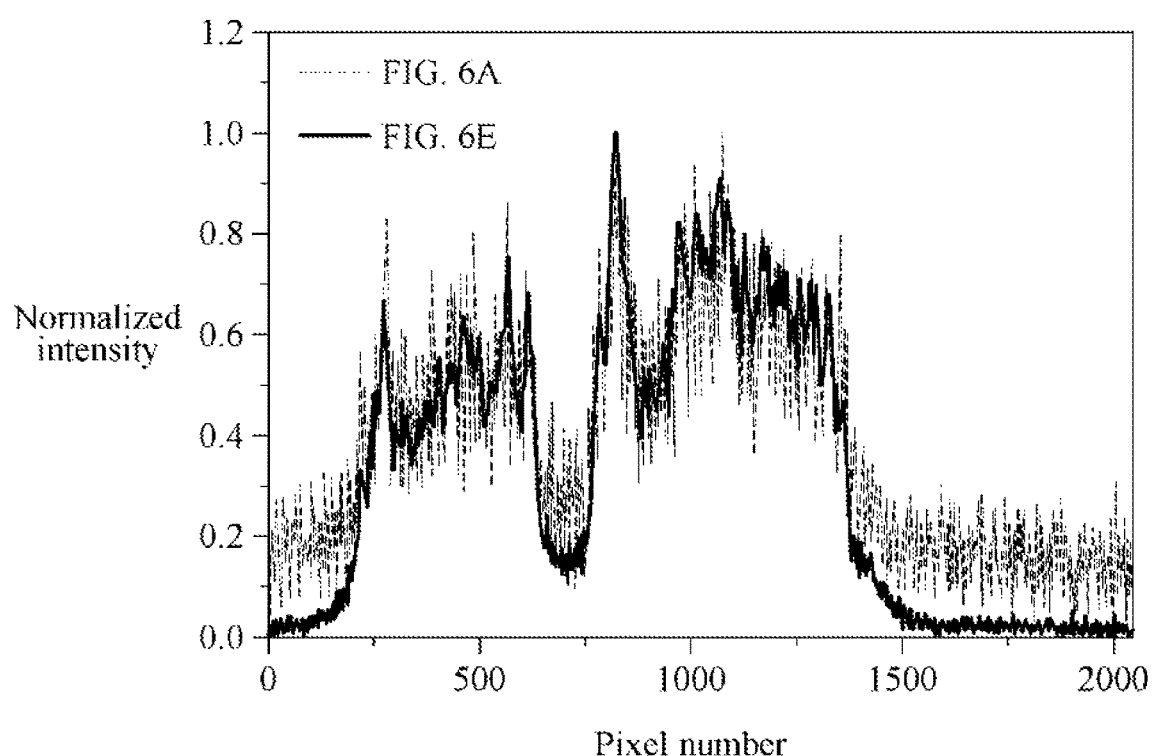
FIG. 7 is a graph illustrating fluorescence intensity profiles detected in FIGS. 6A and 6E.

FIG. 7 is a graph illustrating fluorescence intensity profiles detected in FIGS. 6A and 6E. FIG. 7 illustrates fluorescence intensity profiles of the fluorescence image of FIG. 6A acquired based on the wide-field illumination fluorescence microscopy and the fluorescence image of FIG. 6E acquired based on the four-bucket scheme of the fluorescence image acquisition method. In FIG. 7, the fluorescence image of FIG. 6E has reduced background noise in comparison to the fluorescence image of FIG. 6A. A fluorescence image acquisition apparatus according to an example embodiment may expect an effect of increasing a dynamic range due to the reduced background noise.

Figure 8:
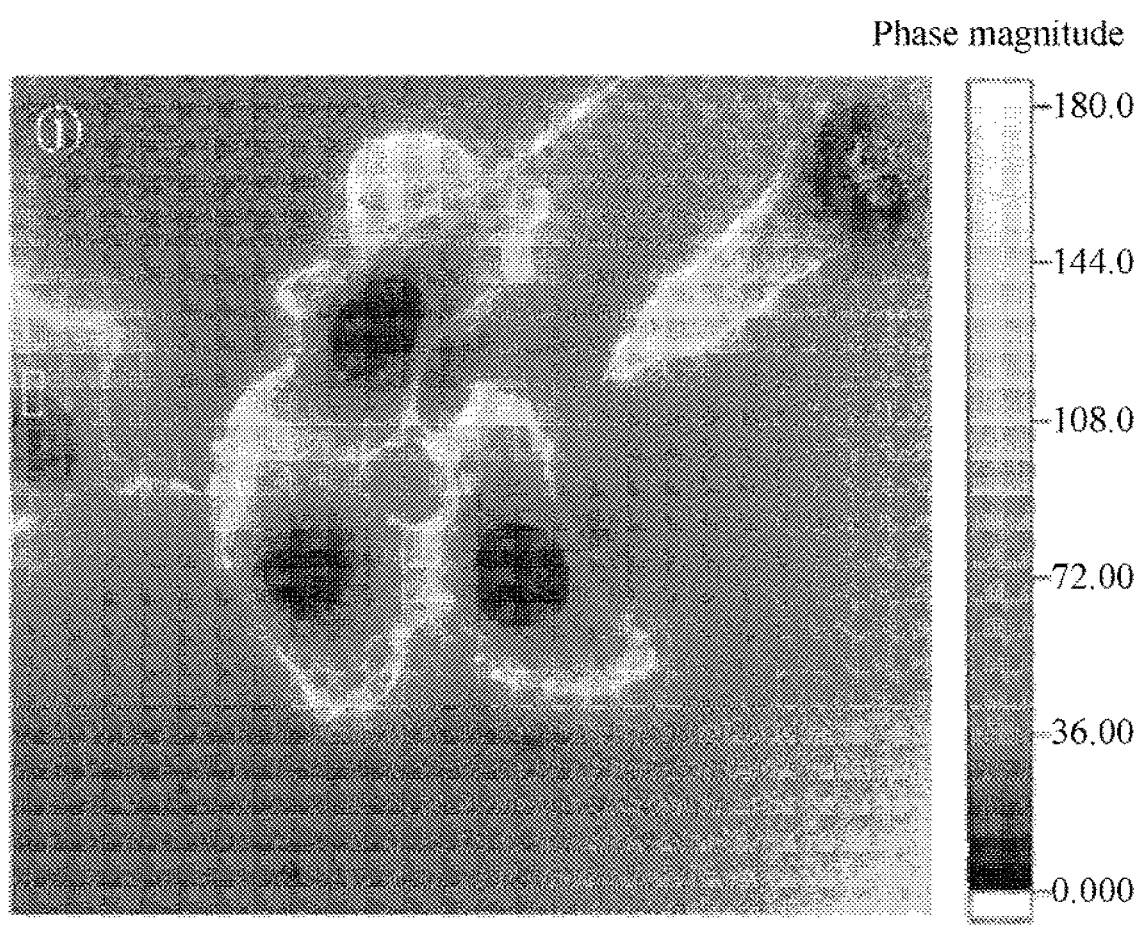
FIG. 8 illustrates an example of a phase image acquired in FIGS. 6E through 6G.

FIG. 8 illustrates a phase image acquired in FIGS. 6E through 6G. The phase image of FIG. 8 represents a great contrast between stained regions in comparison to the fluorescence images of FIGS. 6D and 6H. Also, using the phase image, it is possible to expect an effect of accurately imaging a region that is hardly visible in a fluorescence image due to a low strength of a fluorescence signal.

Figure 9:
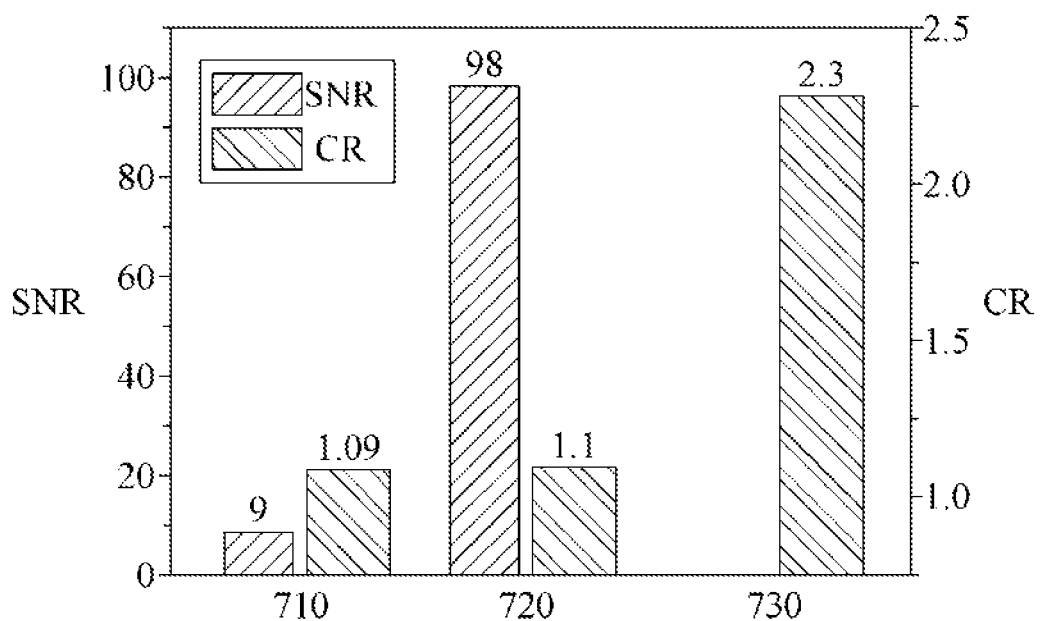
FIG. 9 is a graph illustrating a signal-to-noise ratio (SNR) and a contrast ratio (CR) of a fluorescence image according to an example embodiment in comparison to a related art.

FIG. 9 is a graph illustrating a signal-to-noise ratio (SNR) and a contrast ratio (CR) of a fluorescence image according to an example embodiment in comparison to the related art. Referring to FIG. 9, a fluorescence image 710 acquired based on a wide-field illumination fluorescence microscopy using a specific fluorescence bandpass filter according to the related art, a fluorescence image 720 acquired based on a four-bucket scheme and a phase image 730 corresponding to the fluorescence image 720 are compared in terms of the SNR and CR. An SNR for the fluorescence image 720 is increased at least ten times in comparison to the fluorescence image 710. Also, a CR of the phase image 730 is greater than at least twice those of the fluorescence images 710 and 720.

The example embodiments described above may be implemented using a hardware component, a software component and/or a combination thereof. A processing device may be implemented using one or more general-purpose or special purpose computers, such as, for example, a processor, a controller and an arithmetic logic unit (ALU), a digital signal processor (DSP), a microcomputer, a field-programmable gate array (FPGA), a programmable logic unit (PLU), a microprocessor or any other device capable of responding to and executing instructions in a defined manner. The processing device may run an operating system (OS) and one or more software applications that run on the OS. The processing device also may access, store, manipulate, process, and create data in response to execution of the software. For purpose of simplicity, the description of a processing device is used as singular; however, one skilled in the art will appreciated that a processing device may include multiple processing elements and multiple types of processing elements. For example, a processing device may include multiple processors or a processor and a controller. In addition, different processing configurations are possible, such a parallel processors.

The software may include a computer program, a piece of code, an instruction, or some combination thereof, to independently or collectively instruct or configure the processing device to operate as desired. Software and data may be embodied permanently or temporarily in any type of machine, component, physical or virtual equipment, computer storage medium or device, or in a propagated signal wave capable of providing instructions or data to or being interpreted by the processing device. The software also may be distributed over network coupled computer systems so that the software is stored and executed in a distributed fashion. The software and data may be stored by one or more non-transitory computer readable recording mediums.

The methods according to the above-described example embodiments may be recorded in non-transitory computer-readable media including program instructions to implement various operations of the above-described example embodiments. The media may also include, alone or in combination with the program instructions, data files, data structures, and the like. The program instructions recorded on the media may be those specially designed and constructed for the purposes of example embodiments, or they may be of the kind well-known and available to those having skill in the computer software arts. Examples of non-transitory computer-readable media include magnetic media such as hard disks, floppy disks, and magnetic tape; optical media such as CD-ROM discs, DVDs, and/or Blue-ray discs; magneto-optical media such as optical discs; and hardware devices that are specially configured to store and perform program instructions, such as read-only memory (ROM), random access memory (RAM), flash memory (e.g., USB flash drives, memory cards, memory sticks, etc.), and the like. Examples of program instructions include both machine code, such as produced by a compiler, and files containing higher level code that may be executed by the computer using an interpreter. The above-described devices may be configured to act as one or more software modules in order to perform the operations of the above-described example embodiments, or vice versa.

While this disclosure includes specific examples, it will be apparent to one of ordinary skill in the art that various changes in form and details may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples. Suitable results may be achieved if the described techniques are performed in a different order, and/or if components in a described system, architecture, device, or circuit are combined in a different manner and/or replaced or supplemented by other components or their equivalents. Therefore, the scope of the disclosure is defined not by the detailed description, but by the claims and their equivalents, and all variations within the scope of the claims and their equivalents are to be construed as being included in the disclosure.

What is claimed is:

1. A fluorescence image acquisition apparatus comprising:
    a light source configured to generate, at different time delays, a plurality of optical signals that are modulated at the same frequency;
    an illuminator configured to control paths of the plurality of modulated optical signals so that the plurality of modulated optical signals are illuminated onto a sample comprising a plurality of fluorescent materials;
    a photodetector configured to detect a plurality of fluorescence signals that are emitted from the plurality of fluorescent materials, respectively; and
    a controller configured to acquire a plurality of fluorescence images and a plurality of phase images from the plurality of detected fluorescence signals,
    wherein an intensity value of each pixel in the plurality of phase images is based on a phase magnitude of the plurality of detected fluorescence signals.

2. The fluorescence image acquisition apparatus of claim 1, wherein the controller is configured to acquire a phase image corresponding to each of the plurality of fluorescence signals and configured to separate the fluorescence images for each wavelength corresponding to each of the fluorescence signals based on a fluorescence image comprising the plurality of fluorescence signals.

3. The fluorescence image acquisition apparatus of claim 1, wherein the controller is configured to acquire a fluorescence image comprising the plurality of fluorescence signals and a phase image corresponding to the fluorescence image based on a four-bucket scheme using a frame rate that varies depending on the modulation frequency.

4. The fluorescence image acquisition apparatus of claim 3, wherein the controller is configured to extract a phase image corresponding to each of a plurality of pieces of phase information included in the plurality of fluorescence signals.

5. The fluorescence image acquisition apparatus of claim 1, wherein the photodetector is configured to detect the plurality of fluorescence signals based on a frame rate of 4f when the modulation frequency is f.

6. The fluorescence image acquisition apparatus of claim 1, wherein the illuminator is configured to separate, using a polychroic mirror, the plurality of modulated optical signals generated by the light source and a plurality of fluorescence signals that are emitted from the sample.

7. A method of separating fluorescence images, the method comprising:
    determining whether a fluorescence signal is present, based on a fluorescence image comprising a plurality of fluorescence signals;
    extracting a binary fluorescence image determined based on whether the fluorescence signal is present;
    removing a random phase of a phase image based on the extracted binary fluorescence image;
    extracting, from the phase image from which the random phase is removed, each of phase images separated based on phase information corresponding to each of the fluorescence signals; and
    acquiring multi-wavelength fluorescence images separated based on phase information by applying a fluorescence image comprising a plurality of fluorescence signals to the extracted phase images.

8. The method of claim 7, wherein the fluorescence image comprising the plurality of fluorescence signals is acquired by detecting fluorescence signals generated by illuminating, at different time delays, a plurality of optical signals modulated at the same frequency onto a sample comprising a plurality of fluorescent materials.

9. The method of claim 8, wherein each of the fluorescence signals is modulated after an arbitrary time delay based on the same modulation frequency of a modulated optical signal absorbed by each of the plurality of fluorescent materials.

10. A method of processing fluorescence images, the method comprising:

generating, at different time delays, a plurality of optical signals that are modulated at the same frequency;

controlling paths of the plurality of modulated optical signals so that the plurality of modulated optical signals are illuminated onto a sample comprising a plurality of fluorescent materials;

detecting a plurality of fluorescence signals that are emitted from the plurality of fluorescent materials, respectively; and acquiring a plurality of fluorescence images and a plurality of phase images from the plurality of detected fluorescence signals, wherein an intensity value of each pixel in the plurality of phase images is based on a phase magnitude of the plurality of detected fluorescence signals.

11. The method of claim 10, further comprising:

acquiring a fluorescence image comprising the plurality of fluorescence signals and a phase image corresponding to the fluorescence image based on a four-bucket scheme using a frame rate that varies depending on the modulation frequency.

12. The method of claim 10, further comprising:

acquiring a phase image corresponding to each of the plurality of fluorescence signals and separating fluorescence images for each wavelength corresponding to each of the fluorescence signals based on a fluorescence image comprising the plurality of fluorescence signals.

* * * * *